PHILODENDRON PLANT
Filed Oct. 3, 1975
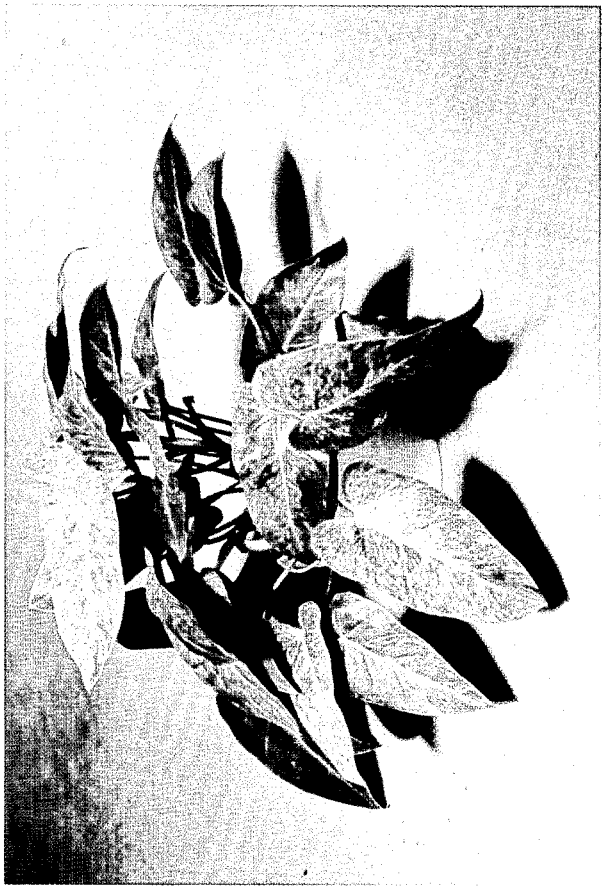

United States Patent

Plant Pat. 3,958

Patented Oct. 19, 1976

3,958

PHILODENDRON PLANT

Robert H. McColley, P.O. Box 17126,
Orlando, Fla. 32810

Filed Oct. 3, 1975, Ser. No. 619,235

Int. Cl.[2] A01H 5/00

U.S. Cl. Plt.—88 1 Claim

ABSTRACT OF THE DISCLOSURE

There is here disclosed a Philodendron plant particularly characterized by the yellow and green mottling of the newer leaves, the leaves as they mature ultimately reaching a state where they appear to be of two shades of green, bright red stems and petioles being further notable identifying aspects of the plant. Where bacterial soft rot and "shot-gun" fungus are encountered, the plant hereof displays a high degree of resistance thereto.

DESCRIPTION OF THE INVENTION

The new and distinct variety of Philodendron plant herein described was hybridized by me in the vicinity of Orlando, Fla., with the result of extensive breeding program which has been carried on by me for many years, the plant being selected and developed from a cross between Philodendron Burgundy (P. Hastatum-Erubescens-Wendlandii-Imbe not otherwise identified) and a variety which I have identified as "Emerald Queen" (unpatented) being a cross which I developed from two unidentified species. This cross last described also produced a variety now patented under Plant Pat. No. 3,502.

This seedling heretofore referred to which produced the Philodendron plant of Plant Pat. 3,502 is apparently a very special species, since it represents a number of distinct Philodendron species as suggested by the references made previously in describing the parentage hereof.

Asexual reproduction of my new variety has been carried out by tip cutting, including removal and rooting of terminal shoots of three or more leaves; other methods of propagation including single eye cuttings, air layering and the use of plunged cane length cuttings has also been effected, the plant in each case developing ultimate plants which run true to form and identified as the new vairety.

My new variety appears to be distinctively different from both of its parents or any other Philodendron of which I have presently any knowledge.

A resistance to bacterial soft-rot which is prevalent in Florida and Gulf Coast areas is outstanding in this particular plant. The plant of my new variety is also virtually immune to the so-called "shot-gun" fungus which as is well known constitutes a rather common dehydration problem.

My new variety displays brilliant colors not available before, the leaf itself being a brilliant yellow and green with stem and petioles of bright red. A sheath covering each new leaf is also bright red, curls back as the leaf unfolds and remains on the plant for weeks.

From the foregoing, it will be understood that the general impression provided by this plant is that there is a group of bright red curls attached to the stem of the plant.

Since it is known that flowering of this type of Philodendron plant is unusual, this aspect is also the same in the instant plant, and as far as I am aware, no flowers of my new variety have ever been observed. In order to develop flowers, ideal environmental conditions would be at least necessary, with plants at full maturity and thus no attempt has been made to develop such flowers.

My new variety exhibits a tendency to climb and when plants of eight leaves or more are involved, these plants will thus require staking as a normal procedure.

The plant grows at a rate which may be termed medium, and under normal greenhouse conditions a young plant develops in three to four months from tip cuttings. Often six to eight months is required to produce a mature plant from the same type of cutting.

The new variety is vigorous, compact and nonbranching; an average plant of five leaves propagated from a tip cutting attaining a height of twelve inches and a spread of eighteen to twenty inches; whereas a five-leaved plant propagated from a single eye cutting may attain a height of eight inches with a spread of twelve to fifteen inches.

Detailed observations from which the description set forth in detail hereinafter was made, were made in my greenhouse in Orlando, Fla. While it is known that significant variations may often occur in accordance with various environmental conditions, including temperature, humidity, day length and available nutrients, where the conditions are consistent, the plants hereof are consistent and run true to form.

My new variety has been found to retain its distinctive characteristics through successive asexual reproduction.

The accompanying drawing forming a part hereof, discloses a typical plant of my new variety, the colors being as nearly true as possible with color illustrations of this type. Color references are made to the Nickerson Color Fan published by Munsell Color Company, with observations being recorded by daylight illumination under vinyl of not more than 50% shade. Comparison and/or contrast may be readily made with the variety of my patented Philodendron plant disclosed in Plant Pat. No. 3,034, the general differences residing in the substantially greater impression of bright red and contrasting colors of leaves.

I. FORM CHARACTERISTICS

1. Leaf shape:
   - (*a*) *Mature.*—Ovate.
   - (*b*) *Immature.*—Ovate.
   - (*c*) *Tip.*—Acute.
   - (*d*) *Base.*—(1) Mature—Auriculate. (2) Immature—Auriculate.
   - (*e*) *Displacement.*—Smooth.
   - (*f*) *Margin.*—Entire.
   - (*g*) *Veination.*—Sunken.
2. Leaf attachment: Stalked.
3. Leaf arrangement: Alternate, horizontal to slightly pendant.
4. Petiole: Long length, erect.
5. Stem: Short, heavy internodes ¾" to 1".
6. Overall appearance: Open.

II. SIZE CHARACTERISTICS OF TYPICAL COMMERCIAL SIZE

1. Leaf itself:
   - (*a*) *Width (widest point).*—5".
   - (*b*) *Width (1" from tip).*—1½".
   - (*c*) *Length.*—8½".
   - (*d*) *Thickness.*—Average.
2. Petiole:
   - (*a*) *Length.*—7".
   - (*b*) *Diameter (center).*—¼".
   - (*c*) *Internode spacing.*—¾"–1".
   - (*d*) *Stem diameter.*—⅝"–¾".

III. COLOR CHARACTERISTICS

1. Leaf (top 6 or 7 leaves):
   (*a*) *Top.*—Green mottled; lighter than 7.5Y 9/8, variations of 10Y 8/11 and 5GY 5/6.
   (*b*) *Bottom.*—Green mottled; lighter than 7.5Y 9/8 variations of 10Y 8/11 and 5GY 5/6.
   (*c*) *Margin.*—Lighter—7.5Y 9/8.
2. Leaf (old bottom leaves):
   (*a*) *Top.*—Green mottled, 5GY 5/6, 7.5GY 4/4.
   (*b*) *Bottom.*—7.5GY 8/7.
   (*c*) *Margin*—Lighter—7.5Y 9/8.
3. Leaf veination:
   (*a*) *Midrib.*—Lighter—7.5Y 9/8.
4. Stem: 2.5R 6/11.

5. Petiole: 2.5R 6/11.

I claim:

1. A new and distinct variety of Philodendron plant substantially as herein disclosed, characterized as to novelty by its yellow, red ang green color contrasts in immature and mature leaves, the bright red color of the sheath covering with tendency to curl back and hang on to the stem for long periods of time, superior growth, resistance to shot-gun fungus and bacterial soft rot.

No references cited.

ROBERT E. BAGWILL, Primary Examiner